US00PP37682P2

(12) United States Plant Patent
Bradford

(10) Patent No.: US PP37,682 P2
(45) Date of Patent: Sep. 8, 2026

(54) ***DELPHINIUM* PLANT NAMED 'DEAZ0002'**

(50) Latin Name: *Delphinium elatum*
Varietal Denomination: DEAZ0002

(71) Applicant: SYNGENTA CROP PROTECTION AG, Basel (CH)

(72) Inventor: Marie Bradford, Foxley Dereham Norfolk (GB)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 19/546,522

(22) Filed: Feb. 23, 2026

(51) Int. Cl.
*A01H 6/72* (2018.01)
*A01H 5/02* (2018.01)

(52) U.S. Cl.
USPC ..... Plt./423

(58) Field of Classification Search
USPC ..... Plt./263.1, 423
See application file for complete search history.

*Primary Examiner* — Karen M Redden
(74) *Attorney, Agent, or Firm* — Dale Skalla

(57) ABSTRACT

A new *Delphinium* plant named 'DEAZ0002', particularly distinguished by its mid pink flowers with a pure white bee (centre), plants are freely basal branching with excellent flower production, compact plants have very uniform upright growth with medium green foliage.

1 Drawing Sheet

Latin name of the genus and species of the plant claimed: *Delphinium elatum.*

Varietal denomination: 'DEAZ0002'.

BACKGROUND OF THE PLANT

The present invention comprises a new *Delphinium*, botanically known as *Delphinium elatum*, and hereinafter referred to by the variety name 'DEAZ0002'.

'DEAZ0002' is a product of a planned breeding program. The new cultivar 'DEAZ0002' has mid pink flowers with a pure white bee (centre), plants are freely basal branching with excellent flower production, compact plants have very uniform upright growth with medium green foliage.

'DEAZ0002' originated from a hybridization made in June 2014, in a greenhouse in Foxley, United Kingdom. The female parent was the unpatented, proprietary breeding line designated as 'DPSCQX', having pale pink flowers with a white bee (center), and being approximately 10 cm shorter in height when compared to 'DEAZ0002'.

The male parent of 'DEAZ0002' was the unpatented, proprietary breeding line designated as 'DPSCQG', having rose pink flowers and a white bee (center), and being approximately 10 cm shorter in height when compared to 'DEAZ0002'.

The seed was sown in January 2021 and the resulting plants were grown in unheated greenhouse conditions in Foxley, Norfolk, UK. 'DEAZ0002' was selected as one flowering plant within the progeny of the stated cross in June 2021.

BRIEF SUMMARY OF INVENTION

Horticultural examination of plants grown via tissue culture reproduced plants of the original plant in April 2023, in Heerhugowaard, The Netherlands, and continuing thereafter, has demonstrated that the combination of characteristics as herein disclosed for 'DEAZ0002' are firmly fixed and are retained through successive generations of asexual reproduction.

'DEAZ0002' has not been observed under all possible environmental conditions. The phenotype may vary significantly with variations in environment such as temperature, light intensity, disease exposure, and day length.

A Plant Breeder's Right for this cultivar was applied for in the European Union on Dec. 18, 2025 and assigned No. 2025/2819. 'DEAZ0002' has not been made publicly available prior to the effective filing date of this application, notwithstanding any disclosure that may have been made less than one year prior to the effective filing date of this application by the inventor or another who obtained 'DEAZ0002' directly from the inventor.

The following traits have been repeatedly observed and are determined to be basic characteristics of the new variety. The combination of these characteristics distinguishes this *Delphinium* as a new and distinct variety.

BRIEF DESCRIPTION OF THE PHOTOGRAPHS

The accompanying photographic drawings shows typical flower and foliage characteristics of 'DEAZ0002' with colors being as true as possible with an illustration of this type.

Figure 1:
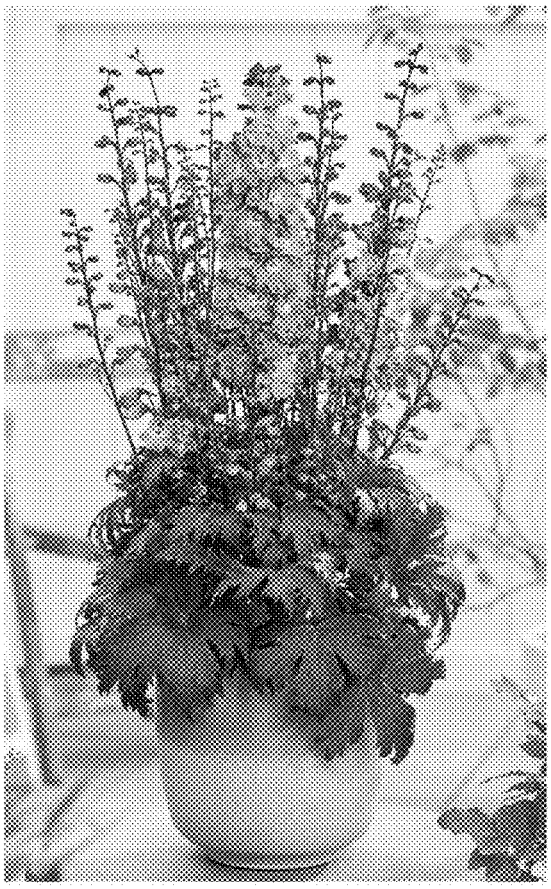

The whole plant photographic drawing, shown in FIG. 1, was taken on Jul. 28, 2023 in Hillegom, The Netherlands.

Figure 2:
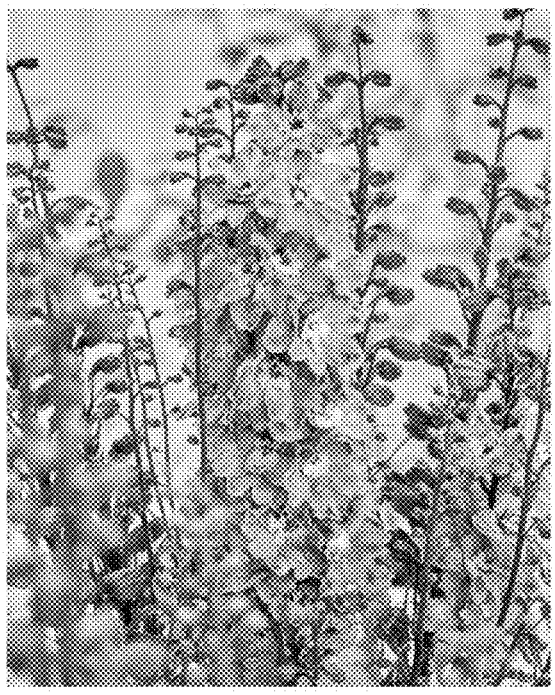

The close-up view of the inflorescence shown in FIG. 2, was taken on Jul. 28, 2023 in Hillegom, The Netherlands.

DETAILED BOTANICAL DESCRIPTION

TABLE 1

DIFFERENCES BETWEEN THE NEW VARIETY 'DEAZ0002' AND A MOST SIMILAR VARIETY

| | 'DEAZ0002' | 'Strawberry Fair', Not patented |
|---|---|---|
| Flower color: | Light pink colored petals with white central bee to each flower. | Medium rose pink color petals with white central bee to each flower. |
| Plant Height: | Height approximately 70 cm | Height approximately 140 cm |
| Plant habit: | Erect stable growth, numerous side shoots | Erect growth, less stable, side shoots develop later |

Growing conditions: Plants used for this description were grown under the following conditions:

*Age of plants used for this description.*—4 months.

*Age and pot size of plants in photos.*—4 months. 19 cm pot.

*Time of year.*—July.

*Container size (if appropriate).*—19 cm circular container.

*Type of greenhouse covering or growing structure.*—Outdoors.

*Physical location (town and country).*—Heerhugowaard, The Netherlands.

*Range or average day temperatures.*—12° C. to 28° C.

*Range or average night temperatures.*—8° C. to 16° C.

*Light levels.*—Normal light level, no additional lighting.

*Photoperiodic treatments.*—No.

*Edition year of R.H.S. Colour Chart used.*—6$^{th}$ edition, 2015.

Plant variety description:

*Annual, biennial, or perennial?.*—Perennial.

*Plant type (tree, shrub, subshrub, vine, cut flower, garden plant and/or potted plant?.*—Herbaceous perennial.

*Crop time.*—Time to flower and/or finishing: Approx. 14 weeks from propagation to saleable plant.

*Appropriate container size and/or cropping system.*—Field grown or in 15 cm pots and larger.

*Overall plant shape.*—Ovate, inflorescences carried above the foliar plane.

*Growth habit.*—Main (flowering) stems grow from base, no lateral branches.

Plant height:

*Soil level to top of foliar plane.*—Average: 33.8 cm.

*Soil level to top of floral plane.*—Average: 70.0 cm.

*Plant diameter or area of spread.*—Average: 42.0 cm.

*Growth rate (low, moderate or high).*—Moderate.

*Plant vigor (low, moderate or high).*—Moderate to high.

*Branching habit.*—No main branches or lateral branches present; flowering stems grow from base.

*Basal branching.*—Yes.

*Pinching required.*—Not necessary.

*Number of primary (main) branches per plant.*—Average: 4 flowering stems.

*Number of secondary (lateral) branches per plant.*—None.

Primary (main) branches (flowering stem):

*Length.*—Average: 22.4 cm (from base to lowest branching of inflorescence).

*Diameter.*—Average: 1.1 cm.

*Internode length.*—Average: 1.9 cm.

Stems:

*Appearance and shape.*—Rounded, very slightly angled; 5-sided.

*Luster.*—Slightly glossy, but covered with a very thin waxy layer; colored green; 138D.

*Aspect/angle from vertical.*—Average angle: 10° (near vertical).

*Strength.*—Strong.

*Color, developing.*—Yellow-green; 146C.

*Color, mature.*—Green; 143C, axially striped yellow-green; 146B.

*Color at internodes.*—Green; 143C, axially striped yellow-green; 146B.

*Color of bark/older stems (if present).*—Not present.

*Pubescence.*—Absent.

Foliage:

*Leaf arrangement.*—Alternate.

*Compound or single.*—Single.

*Number of leaves per main branch.*—Average: 12 stem leaves.

*Whole leaf shape.*—Palmate, broad reniform in outline.

*Whole leaf aspect.*—Slightly concave to slightly convex.

*Whole leaf length.*—Average: 12.3 cm.

*Whole leaf width.*—Average: 15.6 cm.

*Leaf/leaflet apex.*—Narrow acute.

*Leaf/leaflet base.*—Hastate, lobes free.

*Leaf/leaflet margin.*—Coarsely dentate-serrate.

*Leaf/leaflet lobed?.*—Yes, leaves 5-lobed to 7-lobed.

*If lobed, depth of sinuses (deep, medium or shallow).*—Medium to deep.

*Sinus orientation (divergent, parallel or convergent).*—Divergent.

*Leaf/leaflet texture, upper side.*—Smooth, glabrous.

*Leaf/leaflet texture, under side.*—Smooth, glabrous.

*Leaf/leaflet pubescence.*—Both sides glabrous, margins moderately pubescent with very short hairs, average length: 0.3 mm, colored white; too small and too sparsely present to be measured with RHS-CC.

*Leaf/leaflet rugosity.*—Both sides non-rugose.

*Leaf/leaflet luster, upper side.*—Very slightly glossy.

*Leaf/leaflet luster, under side.*—Matte.

*Leaf/leaflet color, young, upper side.*—Green; 143B.

*Leaf/leaflet color, young, under side.*—Yellow-green; a blend of 144A and 146B.

*Leaf/leaflet color, mature, upper side.*—Green; NN137B.

*Leaf/leaflet color, mature, under side.*—Yellow-green; 147B.

*Venation pattern.*—Laciniate.

*Mature leaf venation color, upper side.*—Yellow-green; 144A.

*Mature leaf venation color, under side.*—Yellow-green; 144A.

*Petioles.*—Present.

*Petiole length.*—Average: 12.6 cm.

*Petiole diameter.*—Petiole flattened, average diameter at widest (horizontal): 0.4 cm, average diameter at narrowest (vertical): 0.3 cm.

*Petiole texture.*—Smooth, glabrous.

*Petiole luster*.—Both sides moderately glossy, but covered with a very thin waxy layer, colored yellow-green; 145B.

*Petiole strength* (*high, medium, low*).—High.

*Petiole color, upper side*.—Yellow-green; 144A.

*Petiole color, under side*.—Yellow-green; a blend of 144A and 146A.

*Stipules, tendrils, thorns, spines, prickles*.—Absent.

Inflorescence:

*Arrangement*.—Inflorescence.

*Inflorescence type and form*.—Axillary and terminal raceme.

*Inflorescence height*.—Average: 26.8 cm (from lowest flower to top of inflorescence).

*Inflorescence diameter*.—Average: 6.8 cm.

*Quantity of flowers per inflorescence*.—Average: 20.

*Quantity of flowers per plant*.—Average: 60.

*Quantity of flower buds per plant*.—Average: 220.

*Quantity of flowers and flower buds per plant*.—Average: 280.

*Natural flowering season*.—Midsummer to late summer.

*Time to flower or response time*.—Approximately 9 months.

Flower bud:

*Flower bud length*.—Average: 2.4 cm.

*Flower bud diameter*.—Average diameter horizontally: 1.1 cm, average diameter vertically: 0.9 cm.

*Flower bud shape*.—Obovate, top flattened.

*Flower bud texture*.—Smooth, glabrous.

*Flower bud luster*.—Slightly glossy.

*Flower but color*.—Yellow-green; 145A to 145C, flushed greyed purple; N187B, flower bud tinged green at the top; 143A and 143B.

Flower:

*Flower type and form*.—Rotate, semi-double.

*Flower aspect* (*upright, outwardly, nodding, drooping*).—Outwardly.

*Flowering habit* (*freely, moderate or low*).—Freely.

*Fragrance* (*strength and description*).—No fragrance.

*Flower shape*.—Rotate, semi-double.

*Flower height* (*vertical*).—Average: 5.2 cm.

*Flower diameter* (*horizontal*).—Average: 5.8 cm.

*Flower length* (*depth*).—Average: 3.2 cm.

*Flower longevity on plant*.—Approximately 10 days.

*Flower longevity as a cut flower* (*if applicable*).—Approximately 10 days.

*Persistent or self-cleaning*.—Self-cleaning.

*Tepals*.—No petals and sepals present, only tepals (and tepaloids).

*Tepal arrangement*.—Rotate.

*Tepal number* (*per flower*).—Average: 5, one dorsal tepal, 2 upper lateral tepals and 2 lower lateral tepals.

*Number of tepal whorls*.—Average: 1.

*Tepals fused*?.—No.

*Tepal length*.—Average length of dorsal tepal: 2.9 cm. Average length of upper and lower lateral tepals: 3.0 cm.

*Tepal width*.—Average width of dorsal tepal: 2.2 cm. Average width of upper lateral tepals: 1.7 cm. Average width of lower lateral tepals: 1.8 cm.

*Tepal shape*.—Dorsal tepal ovate. Upper and lower lateral tepals obovate.

*Tepal tip*.—All tepals bluntly acute.

*Tepal base*.—All tepals: broad cuneate.

*Tepal margin*.—All tepals: entire.

*Tepal margin undulation* (*none, low, medium or high*).—In all tepals: low.

*Tepal texture, upper side*.—All tepals: smooth, glabrous, moderately velvety.

*Tepal texture, under side*.—All tepals smooth, glabrous, slightly velvety.

*Tepal rugosity, which side*(*s*).—All tepals, non-rugose.

*Tepal luster, upper side*.—All tepals: matte.

*Tepal luster, under side*.—All tepals: very slightly glossy.

*Tepal color, when opening, upper side*.—Dorsal tepal purple; 76A, fading violet towards the base; 85B and 85D. Upper lateral tepals violet; 84D, fading purple towards the margins and top; 76A, with a small yellow-green blotch near the top; 146B. Lower lateral tepals purple; 76A, fading violet towards the base; 84D, with a small axillary greyed-purple blotch near the top; N187B.

*Tepal color, when opening, under side*.—Dorsal tepal violet; 85A, veined darker; 86C and with a small yellow-green to greyed-green blotch near the top; a blend of 147A and N189A. Upper lateral tepals violet; 84C, fading darker towards the margins and top; 85A, with a small yellow-green blotch near the top; 146B and 146C. Lower lateral tepals purple; 76A and 76B, with a small axillary blotch near the top, yellow-green to violet; a blend of 146B and 86B.

*Tepal color, fully opened, upper side*.—Dorsal tepal violet; 84A, fading violet to greyed-purple towards the base; a blend of 85B and N187B. Upper lateral tepals purple; 76A, fading violet towards the base; 84D. Upper lateral tepals purple; 76A, fading violet towards the base; 84D, with a small axillary violet-blue blotch near the top; 94B.

*Tepal color, fully opened, under side*.—Dorsal tepal violet; 84B, veined darker; 86C and with a small yellow-green blotch near the top; 147A to 147B. Upper lateral tepals violet; 84C to 84D, fading darker towards the margins and top; 84A, with a small yellow-green blotch near the top; 147A to 147B. Lower lateral tepals violet; 84B, fading lighter towards the base; 84D, with a small axillary blotch near the top, violet to greyed-purple; a blend of 86C and N187C.

*Tepal venation, fully opened, upper side*.—No venation visible in tepals.

*Tepal venation, fully opened, under side*.—In dorsal tepals violet; 86C, no venation visible in lateral tepals.

*Tepal color, when fading, upper side*.—Not fading.

*Tepal color, when fading, under side*.—Not fading.

*Tepaloids*.—Present.

*Tepaloid arrangement*.—Rotate.

*Tepaloid number per flower*.—Average: 16. Average number of outer tepaloids: 8. Average number of inner tepaloids: &b 8.

*Number of tepaloid whorls*.—Average: 2, inner whorl of tepaloids often called guard tepaloids or honey tepaloids.

*Tepaloids fused*.—Absent.

*Tepaloid shape*.—Outer tepaloids: narrow elliptic to narrow obovate. Inner tepaloids: oblanceolate to near narrow spathulate.

*Tepaloid length*.—Outer tepaloids average: 2.9 cm. Inner tepaloids average 1.5 cm.

*Tepaloid width*.—Outer tepaloids average: 1.3 cm. Inner tepaloids average 0.5 cm.

*Tepaloid tip*.—Outer tepaloids: bluntly acute. Inner tepaloids: emarginate.

*Tepaloid base*.—Outer tepaloids: cuneate. Inner tepaloids: narrow cuneate.

*Tepaloid margin*.—Outer and inner tepaloids: entire.

*Tepaloid margin undulation* (*none, low, medium or high*).—Outer tepaloids: low, inner tepaloids: none.

*Tepaloid texture, upper side*.—Outer and inner tepaloids: smooth, glabrous, slightly velvety.

*Tepaloid texture, under side*.—Outer and inner tepaloids: smooth, glabrous, slightly velvety.

*Tepaloid rugosity, which side*(*s*).—Outer and inner tepaloids: both sides non-rugose.

*Tepaloid luster, upper side*.—Outer and inner tepaloids: very slightly glossy.

*Tepaloid luster, under side*.—Outer and inner tepaloids: very slightly glossy.

*Tepaloid color, when opening, upper side*.—Outer tepaloids: violet; 84C, fading darker at the top; 84B and fading lighter towards the base; 84D, tinged yellow-green; 144B. Inner tepaloids: yellow-green; 145D, veined darker; 145C.

*Tepaloid color, when opening, under side*.—Outer tepaloids: violet; 84C, fading darker at the top; 84B and fading lighter towards the base; 84D, tinged yellow-green; 144B, and tinged yellow-green near the top; 146D. Inner tepaloids: yellow-green; 145D, veined darker; 145C.

*Tepaloid color, fully opened, upper side*.—Outer tepaloids: violet; 84D, fading darker towards the top; 84C, base tinged yellow-green; 146D. Inner tepaloids: white; 155C, centered yellow-green; 150D.

*Tepaloid color, fully opened, under side*.—Outer tepaloids: violet; 84C, fading darker towards the top; a blend of 84B and 84C, tinged yellow-green near the top and base; 146D. Inner tepaloids: white; 155C, centered yellow-green; 150D.

*Tepaloid venation, fully opened, upper side*.—No venation visible.

*Tepaloid venation, fully opened, under side*.—No venation visible.

*Tepaloid color, when fading, upper side*.—Not fading.

*Tepaloid color, when fading, under side*.—Not fading.

Calyx:

*Calyx shape*.—Rotate.

*Calyx length*.—Average: 3.2 cm (incl. spur).

*Calyx diameter*.—Average diameter horizontally: 5.8 cm, average diameter vertically: 5.2 cm.

Sepals: No petals and sepals present, only tepals (and tepaloids).

*Tepal spurs*?.—Yes, dorsal tepal and dorsal inner tepaloid with a short spur.

*Number of tepal spurs per flower*.—Average: 2.

*Tepal spur length*.—Dorsal tepal spur average: 2.0 cm. Inner tepaloid tepal spur average: 0.9 cm.

*Tepal spur diameter*.—Dorsal tepal spur average: 0.3 cm. Inner tepaloid tepal spur average: 0.15 cm.

*Tepal spur shape*.—In dorsal tepal and in inner tepaloid: narrow oblong.

*Tepal spur apex*.—In dorsal tepal obtuse In inner tepaloid acute.

*Tepal spur base*.—In dorsal tepal and in inner tepaloid: broad cuneate.

*Tepal spur texture*.—In dorsal tepal and in inner tepaloid smooth and glabrous.

*Tepal spur luster*.—In dorsal tepal very slightly glossy. In inner tepaloid glossy.

*Tepal spur color*.—Dorsal tepal spur greyed-purple; N187D, veined darker; N187B. Inner tepaloid spur yellow-green to greyed-green; slightly darker than a blend of 147A and N189A.

*Peduncles*.—Present.

*Terminal peduncle length*.—Average: 34.3 cm.

*Terminal peduncle diameter*.—Average: 0.55 cm.

*Peduncle angle to lateral branch axis*.—Average angle: 0°.

*Peduncle strength*.—Strong.

*Peduncle texture*.—Smooth, glabrous.

*Peduncle luster*.—Moderately glossy, but covered with a very thin waxy layer; colored grey; 201B.

*Peduncle color*.—Yellow-green to greyed-green; a blend of 146A and 197A.

*Pedicels*.—Present.

*Pedicel length*.—Average: 2.3 cm.

*Pedicel diameter*.—Average: 0.1 cm.

*Pedicel angle to peduncle axis*.—Average angle: 20°.

*Pedicel strength*.—Moderately strong.

*Pedicel texture*.—Smooth, glabrous.

*Pedicel luster*.—Glossy.

*Pedicel color*.—Yellow-green; near 146A.

*Floral bracts*.—Present, 2 bracts are near oppositely placed near the distal end of the pedicel, shaped linear, top narrow acute, base narrow cuneate, average length: 1.2 cm, average width: 0.1 cm, smooth, glabrous, upper side green; 137A, under side yellow-green; 147A.

Reproductive organs:

*Number of stamen per flower*.—Average: 22.

*Filament length*.—Average: 0.8 cm, filaments flattened at the base; average width at proximal end: 1.75 mm, average width at distal end: 0.5 mm.

*Filament color*.—White; NN155D.

*Anther shape*.—Oblong.

*Anther length*.—Average: 0.25 cm.

*Anther width*.—Average: 0.1 cm.

*Anther color*.—Green; 136B.

*Amount of pollen* (*none, low, moderate or abundant*).—Low.

*Pollen color*.—White; 155A.

*Pistil number* (*per flower*).—Average: 4.

*Pistil length*.—Average: 0.2 cm.

*Stigma shape*.—Pointed.

*Stigma length*.—Average: 0.1 cm.

*Stigma diameter*.—Average: 0.5 mm.

*Stigma color*.—White; NN155A.

*Style length*.—Average: 0.1 cm.

*Style color*.—White; 155C.

*Ovary color*.—Yellow-green; near 144C.

*Fruit/seeds*.—No fruits/seeds observed to date.

Roots:

*Root structures* (*bulbs, corms, rhizomes*)?—No.

Miscellaneous:

*High temperature tolerance* (° *C*.).—Unknown, at least tolerant to temperatures up to 35° C.

*Low temperature tolerance* (° *C*.).—Unknown, at least tolerant to temperatures up to −23° C

*USDA hardiness zones*.—USDA zone 5 to zone 9.

*Tolerance to rain* (*none, low, moderate or high*).—Moderate.

*Tolerance to wind* (*none, low, moderate or high*).—Low.

*Pest* (*insect or arachnid*) *resistance or tolerance*.—Similar to other *Delphinium* varieties.

*Disease resistance or tolerance*.—Similar to other *Delphinium* varieties.

What is claimed is:

1. A new and distinct variety of *Delphinium* plant named 'DEAZ0002' substantially as illustrated and described herein.

* * * * *